(12) United States Patent
Ko

(10) Patent No.: US 6,178,229 B1
(45) Date of Patent: Jan. 23, 2001

(54) MOUTH HELD PLATE FOR USE IN TOMOGRAPH

(76) Inventor: Shen-Po Ko, 6 Floor, No.143, Sec. 3 Chen-Kong Road, Taipei (TW)

( * ) Notice: Under 35 U.S.C. 154(b), the term of this patent shall be extended for 0 days.

(21) Appl. No.: 09/192,361

(22) Filed: Nov. 16, 1998

(51) Int. Cl.$^7$ ..................................................... H05G 1/28
(52) U.S. Cl. .............................................................. 378/164
(58) Field of Search ..................................... 378/164, 205

(56) References Cited

U.S. PATENT DOCUMENTS 3,770,956 * 11/1973 Johnson .................................. 378/164

* cited by examiner

Primary Examiner—Craig E. Church
(74) Attorney, Agent, or Firm—Bacon & Thomas

(57) ABSTRACT

A mouth held plate for use in tomography is divided into two portions, a gum-shaped inner plate and an arc-shaped symmetric outer plate that are integrally connected to each other. A plurality of cavities for holding a molding substance are disposed on the inner plate, and the inner plate is connected to the outer plate at the middle point thereof. The outer plate is provided with a horizontally calibrated x-axis and a vertically calibrated y-axis are accompanied with a grid-marked area respectively. A square hole is disposed adjacent the x-axis on the outer plate for mounting a camera which can take tomograms by consecutive exposures under X-rays. The inner plate is held by the mouth of a patient and bitten by the teeth of the patient at the same time so as to keep the dental data of the patient recorded on the molding substance when it becomes solidified. Such a recording plate permits a spot in the mouth under scrutiny to be precisely pin pointed with the help of the coordinates set by the x-axis and y-axes on the outer plate. Thus, the recording plate can eliminate the positional misalignments produced in the procedure of tomography as a result of careless movement in operation and mistaken measurement caused by the blockage of facial muscles.

2 Claims, 4 Drawing Sheets

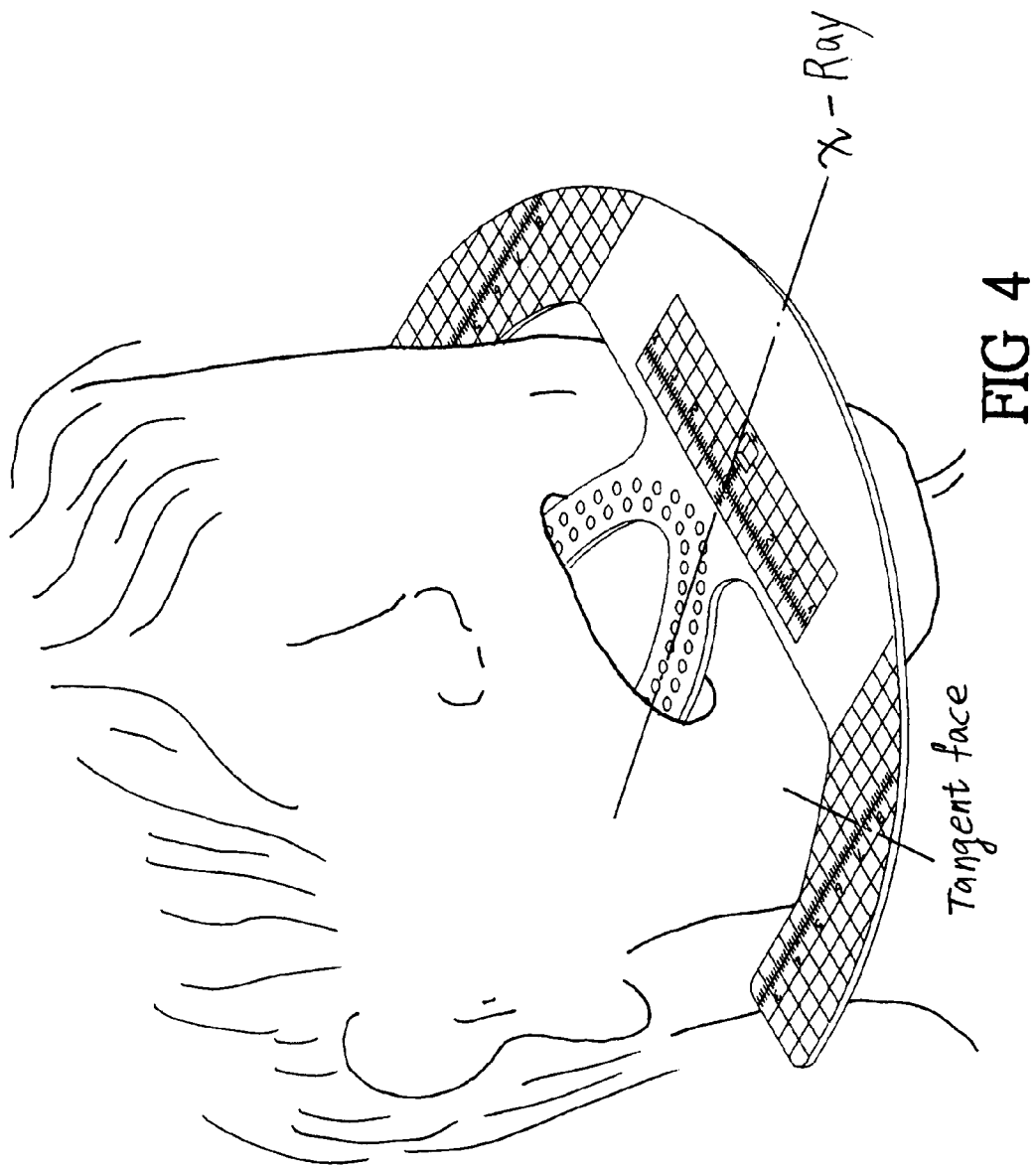

MOUTH HELD PLATE FOR USE IN TOMOGRAPH

BACKGROUND OF THE INVENTION

The present invention relates to a mouth held plate for use in tomography. The plate can be divided into two portions, a gum-shaped inner plate and an arc-shaped symmetric outer plate that are integrally connected to each other. A plurality of cavities for holding a molding substance are disposed on the inner plate, the inner plate is connected to the outer plate at the middle point thereof. The outer plate is provided with a horizontally calibrated x-axis and a vertically calibrated y-axis at each side of the symmetric arc-shaped outer plate. The x-axis and y-axes are accompanied with a grid-marked area respectively. A square hole is disposed adjacent the x-axis on the outer plate for mounting a camera which can take tomograms by consecutive exposures under X-rays. The inner plate is held by the mouth of a patient and bitten by the teeth of the patient at the same time so as to keep the dental data of the patient recorded on the molding substance when it becomes solidified. Such a recording plate permits a spot in the mouth under scrutiny to be precisely pin pointed with the help of the coordinates set by the x-axis and y-axes on the outer plate. Thus, the plate can eliminate the positional misalignments produced in the procedure of tomography as a result of careless movement in operation and mistaken measurement caused by the blockage of facial muscles.

An improved mouth held plate intends to eliminate the conventional problems in the operational procedures of dental diagnosis and analysis by tomography, such as positional misalignments and visual blockage by facial muscles in precise setting of the coordinates of a point in the mouth of a patient.

In general, in conventional tomography, a mounting plate put in the mouth of a patient is commonly used to facilitate the pin pointing of a spot in the mouth of a patient under scrutiny. The patient with the mounting plate held in mouth is positioned in front of a tomograph for taking consecutive tomograms exposed under X-rays at a computer set mean interval for diagnosis or examination by tomography.

Such convention procedures and the tools used in tomography seem acceptable. However, there are still some disadvantages as follows.

1. Positional misalignments are easily produced as a result of the visual blockage to the correct coordinates of a point in a patient's mouth; the positional misalignments produced in the patient's consecutive positioning in front of a tomograph every time; a computer set mean value being not suit for all people under scrutiny because of difference in the width of jaws of patients. So, positional misalignments are easily produced in consecutively exposed tomograms, making the tomograms poor to read in practice.
2. The operational procedures are tedious, time wasting and the cost of such tomography is relatively high as a result of the positional misalignments making the computer taken consecutive tomograms hard to locate correct coordinates. In such a case, repeated alignments, photo shootings inevitably cause waste of time, material, resulting in raise of cost. Besides, consecutive tomograms cause controversy in selection of one proper picture for use.
3. The operation can cause harm to a human body. Even tomography is widely adopted in the dental transplantation because it can provide for an elevation image for analysis before a surgery and for follow-up after a surgery so as to help avoid damage to important physical dissection structure. However, improper tomograms become helpless and can even cause harmful aftermath to a patient if mistakes are not eliminated in advance.

SUMMARY OF THE INVENTION

Therefore, the primary object of the present invention is to provide for an improved mouth held plate for use in tomography which can make the operational procedures simple, accurate and time saving by means of a horizontal x-axis and vertical y-axes on the outer plate which can effectively eliminate positional misalignments in dental transplantation due to careless movements.

Another object of the present invention is to provide for an improved mouth held plate which make precise one spot tomograph possible without using consecutive X-ray exposed tomograms in a trial and error approach so as to reduce mistakes and save time and cost.

One further object of the present invention is to provide an improved mouth held plate, which can be easily adapted to various types of tomograph.

BRIEF DESCRIPTION OF THE DRAWINGS

FIG. 4 is a perspective diagram showing the practical application of plate to a patient under scrutiny of tomography.

DETAILED DESCRIPTION OF THE PREFERRED EMBODIMENT

The present invention provides for an improved mouth held plate adapted for use in tomography applied to a dental diagnosis and analysis. It intends to eliminate the positional misalignments produced in patient and instrumental arrangement and the visual blockage caused by facial muscles.

Figure 1:
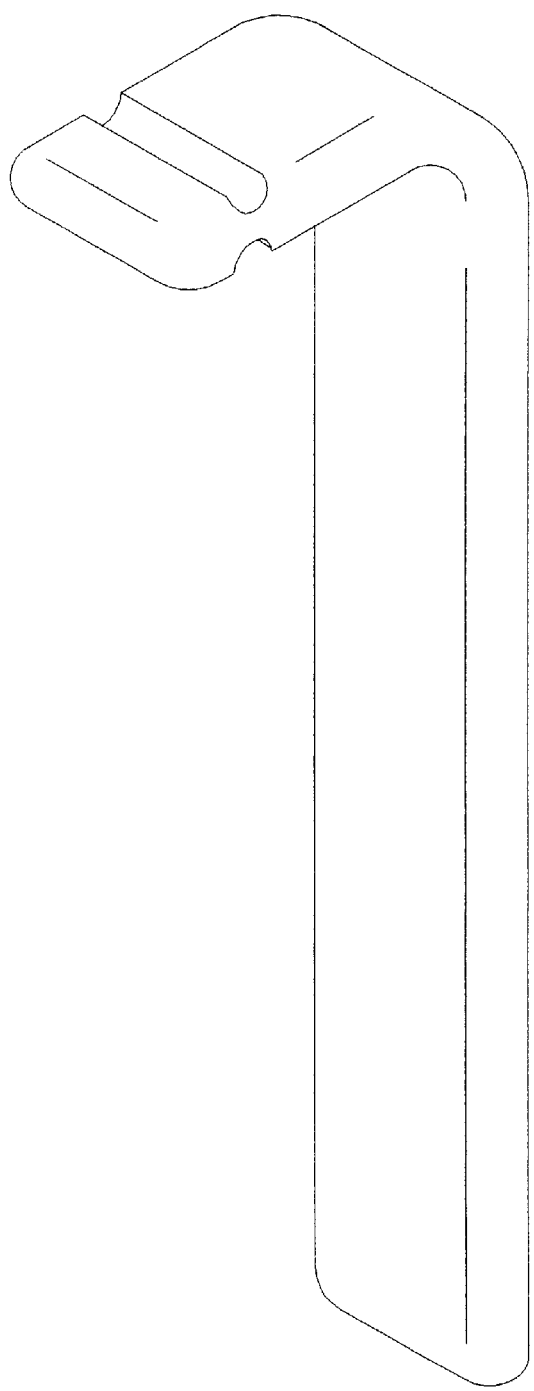
FIG. 1 is a diagram showing a conventional tool used in tomography.
Figure 2:
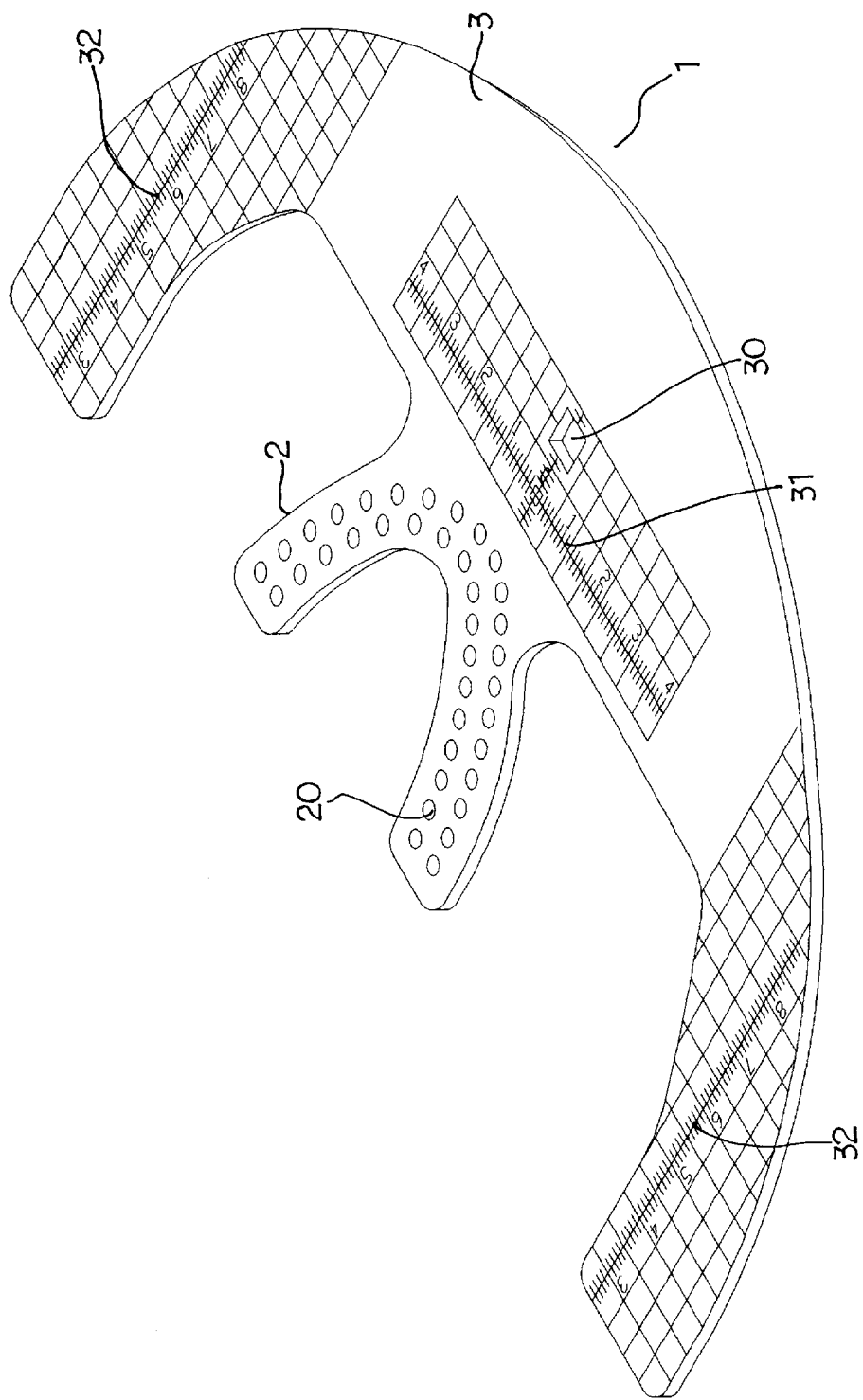
FIG. 2 is a perspective diagram showing the structure of the plate of the present invention.
Figure 3:
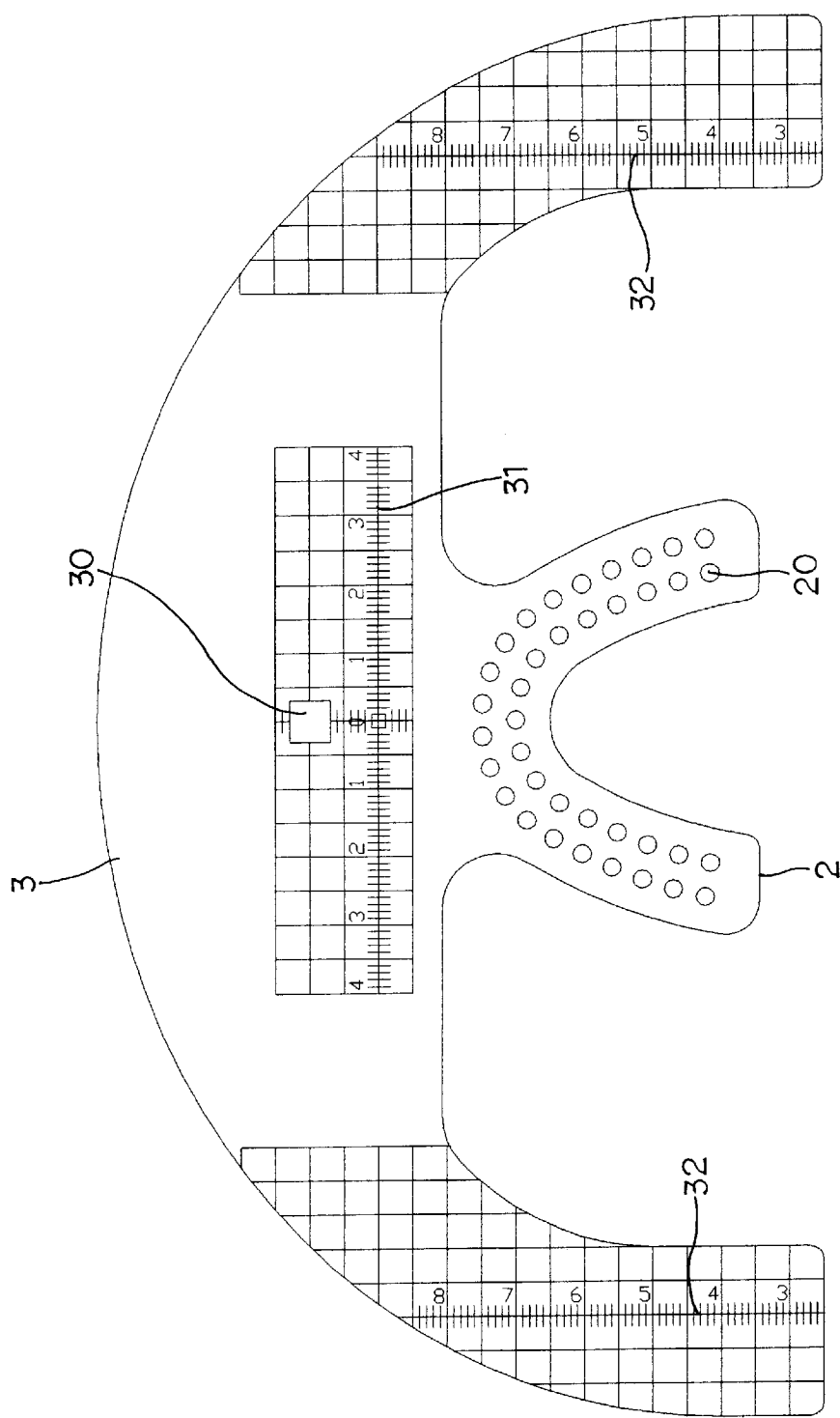
FIG. 3 is a top elevation view of the plate thereof.

Referring to FIGS. 2, 3, the mouth held plate 1 of the present invention comprises a flat inner plate 2 and a flat outer plate 3 that are integrally connected to each other. The flat inner plate 2 made in a gum-shaped form with a plurality of consecutive cavities 20 defined thereon has a size in such a manner that the inner plate 2 can be fitly placed in the mouth of a patient. In the cavities 20 is filled a molding substance, which can keep track of the dental arrangement of the patient in one aspect and can retain the dental jaw in another aspect.

The outer plate 3 made of a symmetric arc-shaped form having a middle point to which said gum-shaped inner plate is extendedly connected. A square hole 30 is disposed adjacent said middle point of connection for mounting of a camera which is used to take tomograms exposed by consecutive X-rays.

On the outer plate is disposed a horizontally calibrated x-axis 31 adjacent said square hole 30 of the arc-shaped outer plate 3 which has two symmetric sides on each of which is provided with a vertically calibrated y-axis 32. Both the x-axis 31 and y-axes 32 are accompanied with a grid marked area.

Referring to FIG. 4, at the beginning of tomography, the cavities 20 of the inner plate 2 of the mouth held plate 1 is first filled with a molding substance. Then the inner plate 2 is held by the mouth of a patient and bitten by the teeth of the patient so as to permit the patient's personal dental data to be recorded by the molding substance when it becomes solidified. At the time, a central point to be subject to tomography examination is to be determined and pin pointed by its coordinates set by the x-axis and y-axes. By way of this central point, a slice plane through the central point and its tangent can be well defined.

Both planes are extended to the outer plate 3. The physical meaning of the slice plane and its tangent plane for the trajectory of the movement of a negative and the shooting direction of X-ray getting the negative exposed in operation whereby a precise tomogram can be taken easily.

In summary, a point under scrutiny in the mouth of a patient can be precisely positioned by reading a coordinate of the spot of its x-axis and y-axis on the outer plane outside the mouth of the patient, making a one shot tomography possible by eliminating the visual blockage of facial muscles to pin point the coordinates of the spot in the mouth and avoiding positional misalignment in the process of arrangement of the patient with respect to a tomograph. It enables a tomograph not only to be operated with precision but also with facility.

In addition, the mouth held plate can be adapted easily to conform to various types of tomographs by merely changing the calibrations on the x-axis and y-axes.

I claim:

1. A mouth held plate for use in tomography, comprising:
   a flat inner plate and a flat outer plate that are integrally connected to each other;
   said inner plate of a gum-shaped form having a plurality of cavities defined thereon;
   said outer plate made of a symmetric arc-shaped form having a middle point to which said gum-shaped inner plate is connected;
   a square hole being disposed adjacent said middle point of connection for mounting of a camera which is used to take tomograms exposed by consecutive X-rays;
   on said outer plate being disposed a horizontally calibrated x-axis adjacent said square hole of said outer plate;
   said arc-shaped outer plate having two symmetric sides on each of which is provided with a vertically calibrated y-axis;
   said x-axis being accompanied with grid marked area;
   said y-axis being accompanied with grid marked area;
   said inner plate for being held by the mouth of a patient and bitten by the teeth of said patient so as to permit a personal dental data to be recorded by said solidified molding substrate;
   whereby a spot under scrutiny in the mouth of said patient that can be precisely positioned by reading a coordinate of said spot of its x-axis on said outer plate outside the mouth of said patient, making a one shot tomography possible.

2. The mouth held plate as claimed in claim 1 wherein said calibrations on said x-axis and y-axes are variably adjusted in conformance to various types of tomograph used.

* * * * *